United States Patent [19]

Harnisch

[11] Patent Number: 4,614,713
[45] Date of Patent: Sep. 30, 1986

[54] FLUOROGENIC PHOSPHATE ESTERS OF HYDROXY-PYRENE-SULFONIC ACIDS FOR FLUORIMETRIC DETERMINATION OF PHOSPHATASES

[75] Inventor: Horst Harnisch, Much, Fed. Rep. of Germany

[73] Assignee: Bayer Aktiengesellschaft, Leverkusen, Fed. Rep. of Germany

[21] Appl. No.: 787,889

[22] Filed: Oct. 16, 1985

Related U.S. Application Data

[62] Division of Ser. No. 572,722, Jan. 20, 1984.

[30] Foreign Application Priority Data

Feb. 5, 1983 [DE] Fed. Rep. of Germany ....... 3303871

[51] Int. Cl.$^4$ ............................................. C12Q 1/42
[52] U.S. Cl. ..................................... 435/21; 558/196
[58] Field of Search ........................... 260/947; 435/21

[56] References Cited

U.S. PATENT DOCUMENTS 2,071,354  2/1937  Morgan ............................... 260/947
4,277,561  7/1981  Monget et al. ........................ 435/21

FOREIGN PATENT DOCUMENTS 3303871  8/1984  Fed. Rep. of Germany .

*Primary Examiner*—Christine M. Nucker
*Assistant Examiner*—William J. Herald
*Attorney, Agent, or Firm*—Sprung, Horn, Kramer & Woods

[57] ABSTRACT

Compounds of the formula

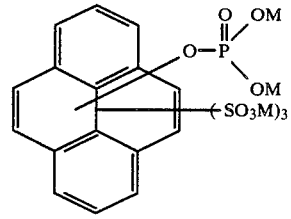

in which
  M each independently is hydrogen, an alkali metal ion, an ammonium ion, or an ammonium ion substituted by up to four $C_1$ to $C_5$-alkyl and/or hydroxyalkyl radicals, are fluorogenic and suitable for the fluorimetric determination of phosphatases.

6 Claims, No Drawings

FLUOROGENIC PHOSPHATE ESTERS OF HYDROXY-PYRENE-SULFONIC ACIDS FOR FLUORIMETRIC DETERMINATION OF PHOSPHATASES

This is a division of application Ser. No. 572,722 filed Jan. 20, 1984, now pending.

The invention relates to new fluorogenic and readily water-soluble esters of phosphoric acid which, on exposure to phosphatases, form a highly fluorescent colored anion and can be used for an advantageous method of determination of phosphatases.

Fluorimetric procedures for the determination of phosphatase activities have already been known for a considerable time (Guilbault, Enzymatic Methods of Analysis, Pergamon Press 1970). Fluorimetry is so sensitive that, using it, it is possible to detect and determine even extremely low concentrations of enzymes. Known phosphatase reagents used for fluorimetry are phosphoric esters of umbelliferone (G. G. Guilbault et al., Anal. Letters 1 (1968) 333), of 4-methylumbelliferone (H. N. Fernley, P. G. Walker, Biochem. J. 97 (1965) 95), of flavonol (D. B. Land, E. Jakim, Anal. Biochem. 16, (1966) 481), of α-naphthol (D. W. Moss, Clin. chim. Acta 5', (1960) 283), of β-naphthol (L. J. Greenberg, Biochem. Biophys. Res. Comm. 9 (1962) 430) and of 3-0-methylfluorescein (H. D. Hill et al., Anal. Biochem. 24 (1968) 9).

All these reagents are soluble in water to only a very limited extent.

The object of the present invention is to make available reagents for the fluorimetric detection and determination of phosphatases, which reagents have a considerably better solubility in water. This object is achieved by using the esters of phosphoric acid according to the invention.

The invention relates to new esters of phosphoric acid of the formula

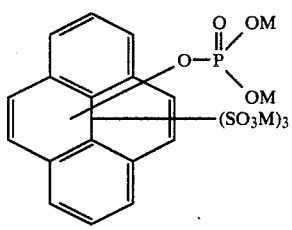

(I)

in which
the radicals M are identical or different and represent hydrogen, an alkali metal ion or an ammonium ion which can be substituted by 1-4 $C_1$ to $C_5$-alkyl radicals, preferably $C_1$ to $C_3$-alkyl radicals, which optionally contain a hydroxyl group.

According to the invention, esters of phosphoric acid of the formula

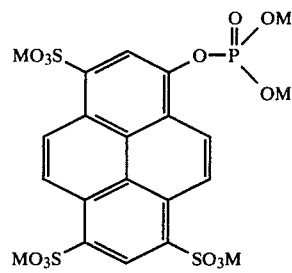

are preferred.

The esters of phosphoric acid of the formula (I) according to the invention can be prepared by, in the first place, reacting hydroxyl compounds of the formula

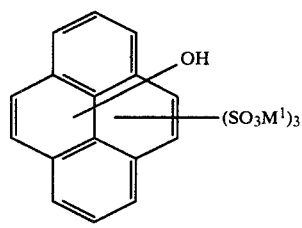

(II)

preferably those of the formula

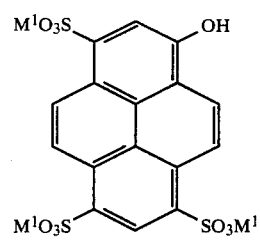

in which
the radicals $M^1$ are identical or different and represent hydrogen or an alkali metal ion or ammonium ion,
with a phosphorus pentahalide, such as phosphorus pentachloride or pentabromide, in a molar ratio of, preferably, about 1:3 to 1:5, and then hydrolyzing the dihalogenophosphonyloxy compound obtained.

The reaction is preferably carried out in the presence of a solvent or diluent in the temperature range from −5° to 100° C., preferably at 20°–90° C.

Suitable solvents and diluents are organic liquids which are inert under the reaction conditions, such as toluene, chlorobenzene, dichlorobenzene, dichloromethane, chloroform, tetrachloromethane, dichloroethane, dichloropropane, trichloroethylene, acetonitrile, dioxane or tetrahydrofuran.

The hydrolysis of the intermediate dihalogenophosphonyloxy compounds to give I can be carried out, for example, by carefully warming to about 50° C. with water, but it can be carried out under milder conditions at temperatures of 0°–25° C. by neutralization with alkali metal hydroxide or alkali metal carbonate solution or aqueous ammonia, amines or ammonium hydroxides. The alkali metal or ammonium salts obtained are then evaporated to dryness in vacuo.

Examples of suitable amines are dipropylamine, dibutylamine, triethylamine, trimethylamine, tripropylamine, tributylamine, diethanolamine, N-methyldiethanolamine, triethanolamine, propanolamine, dipropanolamine and tripropanolamine. Ammonium hydroxides which may be mentioned are tetramethylammonium, tetraethylammonium, tetrapropylammonium and tetrabutylammonium hydroxide.

The acid form, (I) with M=H, is advantageously obtained by filtering the aqueous solution of the alkali metal or ammonium salt through an acid ion exchanger column and, if desired, evaporating the solution obtained.

The hydroxypyrenetrisulphonic acids (II) to be used as starting compounds in the process according to the invention can be prepared in a manner known per se by tetrasulphonation of pyrene and subsequent alkali fusion, and can be obtained commercially under the name Pyranin$^{(R)}$.

The new compounds of the formula (I) are water-soluble substances which have only pale colors and which, in an aqueous medium, are cleaved by alkaline or acid phosphatase to give the highly fluorescent anion of (II) which has an intense yellow color.

The new phosphatase reagents of the formula (I) are suitable for the direct detection of phosphatases in biological materials. It is possible to use them particularly advantageously for the quantitative fluorimetric determination of alkaline or acid phosphatases in clinical analysis.

They can be used for the determination of the activity of phosphatases in a wide variety of body fluids (serum, cerebrospinal fluid or urine). However, it is also possible to employ the reagents according to the invention, in analogy to the teaching of U.S. Pat. No. 3,772,340, for the measurement of the concentration of bacteria in fluids (for example urine infected with bacteria). For this purpose, in the first place, in a manner known per se (for example osmometric shock or formation of spheroplasts) the bacterial enzymes, including the phosphatases, are liberated. It is then possible to draw conclusions about the number of bacteria present from the phosphatase activity determined using the compounds according to the invention.

In the determination of the phosphatase activity, the compounds according to the invention, because of their excellent water-solubility, can be employed in the form of aqueous solutions, optionally buffered to the desired pH (for example about 4.5-7 for acid phosphatases, and about 7-10 for alkaline phosphatases). However, it is also possible to apply the new esters of phosphoric acid to a support in a manner known per se and to allow the detection reaction to take place in a heterogeneous phase. Examples of suitable support materials air filter paper or silicon dioxide which has been applied to an artificial material (for example polystyrene) and provided with an organic binder. It is possible in this manner to produce test strips which start to fluoresce after the fluid to be investigated has been applied, and the fluorescence of which can be measured using a fluorimeter customary in clinical analysis. Quantitative determination of the phosphatase activity in an unknown sample is possible when the time course of the fluorescence intensity in the aqueous solution or on the test strip is compared with that of standards having a known phosphatase content.

In the experiments which are described below, the standards used were the following phosphatase preparations supplied by Sigma Chemical Co.:

(a) alkaline phosphatase (EC 3.1.3.1):

type I-S (P7640)
(from bovine testicular mucosa)
(b) acid phosphatases (EC 3.1.3.2):
type III (P6760)
type IV-S (P1146)
type V (P1267)
(from wheat germ, potatoes, milk and bovine testes).

EC is the term used for the enzyme catalogue which is valid internationally.

EXAMPLE 1

50 g (0.24 mole) of phosphorus pentachloride are introduced, at 20°-30° C. with cooling and stirring and exclusion of moisture, into 400 ml of dry acetonitrile, and then 21 g (0.04 mole) of trisodium 6-hydroxy-1,3,8-pyrenetrisulphonate are introduced at the same temperature, and the mixture is stirred without further cooling for 20 hours. The resulting solution is discharged onto 750 ml of icewater. The pH is adjusted to 7 by dropwise addition of about 108 g of 45% strength sodium hydroxide solution (1.2 moles), the solution is left to stand for 20 hours, filtered, and the filtrate is evaporated using a rotary evaporator at 40° C. bath temperature under waterpump vacuum. The residue is extracted with 400 ml of methanol at boiling temperature for 15 hours, filtered and the filtrate is evaporated again at 40° C. under vacuum. There are obtained 29.8 g of a pale yellowish crystalline powder which is highly soluble in water and contains, in addition to a little NaCl and sodium phosphate, the compound of the following formula as the major constituent:

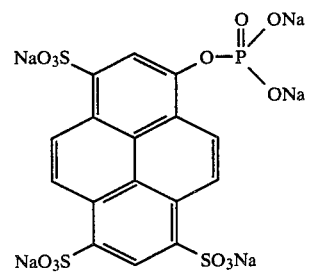

The corresponding K or ammonium salts are prepared in an analogous manner using aqueous KOH or aqueous ammonia or an aqueous solution of triethanolamine.

In order to follow enzymatic hydrolysis by phosphatases, excitation in the fluorimeter is at about 450 nm and the extinction at 495 nm is measured.

EXAMPLE 2

The cell of a fluorimeter is filled at 23° C. with 3 ml of a 0.1 molar aqueous citrate-buffered (0.05 mole of citrate per liter) solution of the Na salt according to Example 1, of pH 7.8, the excitation wavelength is set at 450 nm and the emission wavelength is set at 495 nm, 0.1 ml of the body fluid (serum or cerebrospinal fluid) which is to be determined for acid phosphatase activity and the content of which should be of the order of 0.1 mg of phosphatase per ml, is added, and the change of the fluorescence intensity with time is followed over a period of about 1 to 3 min and compared with previously constructed calibration curves. The initial linear rise in fluorescence intensity is a direct measure of the enzyme activity. The detection limit for phosphatases with the procedure described above is about $1 \times 10^{-5}$ enzyme units per ml.

Phosphatase from bovine testicular mucosa (enzyme catalogue No. 3.1.3.1, type I-S), which can be obtained commercially from Sigma Chemical Co., No. p-7640, can be used as the calibration substance.

It will be appreciated that the instant specification and examples are set forth by way of illustration and not limitation, and that various modifications and changes may be made without departing from the spirit and scope of the present invention.

I claim:

1. A composition suitable for the determination of phosphatase activity comprising a fluorimetrically detectable amount of a compound of the formula

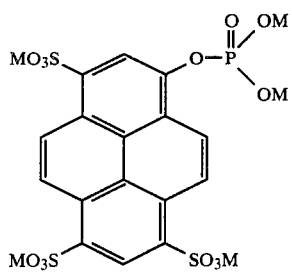

in which
M each independently is hydrogen, an alkali metal ion, an ammonium ion, or an ammonium ion substituted by up to four $C_1$ to $C_5$-alkyl and/or hydroxyalkyl radicals,
in admixture with a diluent.

2. A composition according to claim 1, wherein the diluent comprises water in which the compound is dissolved.

3. A composition according to claim 1, wherein the diluent comprises a solid support which carries the compound.

4. A composition according to claim 1, wherein M is selected from the group consisting of Na, K and $NH_4^+$.

5. In the determination of phosphatase activity in a liquid sample wherein the sample is contacted with a fluorogenic compound and the degree of fluorescence of the sample plus compound is determined with the passage of time, the improvement which comprises employing as the fluorogenic compound a compound of the formula

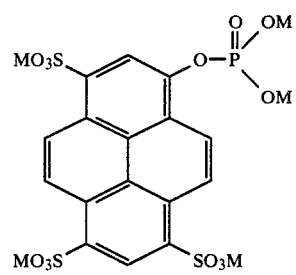

in which
M each independently is hydrogen, an alkali metal ion, an ammonium ion, or an ammonium ion substituted by up to four $C_1$ to $C_5$-alkyl and/or hydroxyalkyl radicals.

6. A method according to claim 5, wherein M is selected from the group consisting of Na, K and $NH_4^+$.

* * * * *